United States Patent [19]

Mookherjee et al.

[11] 3,991,123
[45] Nov. 9, 1976

[54] TETRACYCLIC ALCOHOLS

[75] Inventors: Braja Dulal Mookherjee, Matawan; Robert Walter Trenkle, Bricktown; Kenneth K. Light, Long Branch, all of N.J.; Edward J. Shuster, Brooklyn, N.Y.

[73] Assignee: International Flavors & Fragrances Inc., New York, N.Y.

[22] Filed: Sept. 17, 1975

[21] Appl. No.: 614,077

Related U.S. Application Data

[63] Continuation-in-part of Ser. No. 482,214, June 24, 1974, abandoned.

[52] U.S. Cl. .............................. 260/617 F; 252/42; 252/89 R; 252/132; 252/173; 252/522; 260/586 C; 260/586 G; 260/617 R
[51] Int. Cl.² .......................................... C07C 35/22
[58] Field of Search ..................... 260/617 R, 617 F

[56] References Cited
UNITED STATES PATENTS
3,925,486   12/1975   Greuter et al. .................. 260/617 F

OTHER PUBLICATIONS

Corey et al., 166 "Science" 178,1969 Computer Assisted Design of Complex Organic Syntheses

*Primary Examiner*—Norman Morgenstern
*Attorney, Agent, or Firm*—Arthur L. Liberman; Harold Haidt; Franklin D. Wolffe

[57] ABSTRACT

Described is a genus of novel compounds, defined by the generic structure:

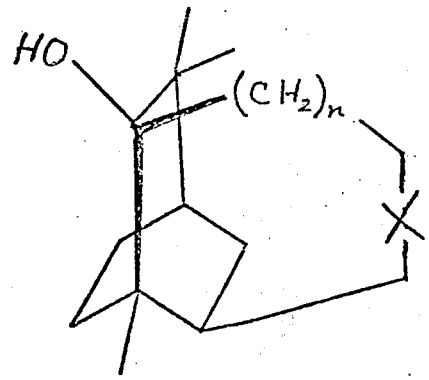

wherein $n$ is 0 or 1 and X is selected from the group consisting of 1,2-cyclo-propylene having the structure:

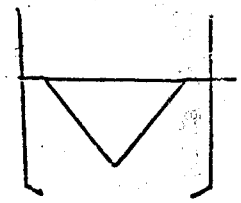

and 1,2-ethenylene having the structure:

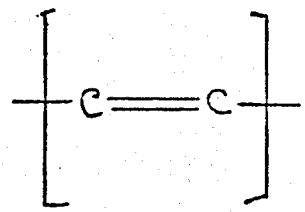

X being cyclopropylene when $n$ is 1, useful for altering, enhancing, modifying or imparting an aroma of or to consumable products including perfumes, perfume comositions and perfumed articles.

5 Claims, 3 Drawing Figures

Figure 1:
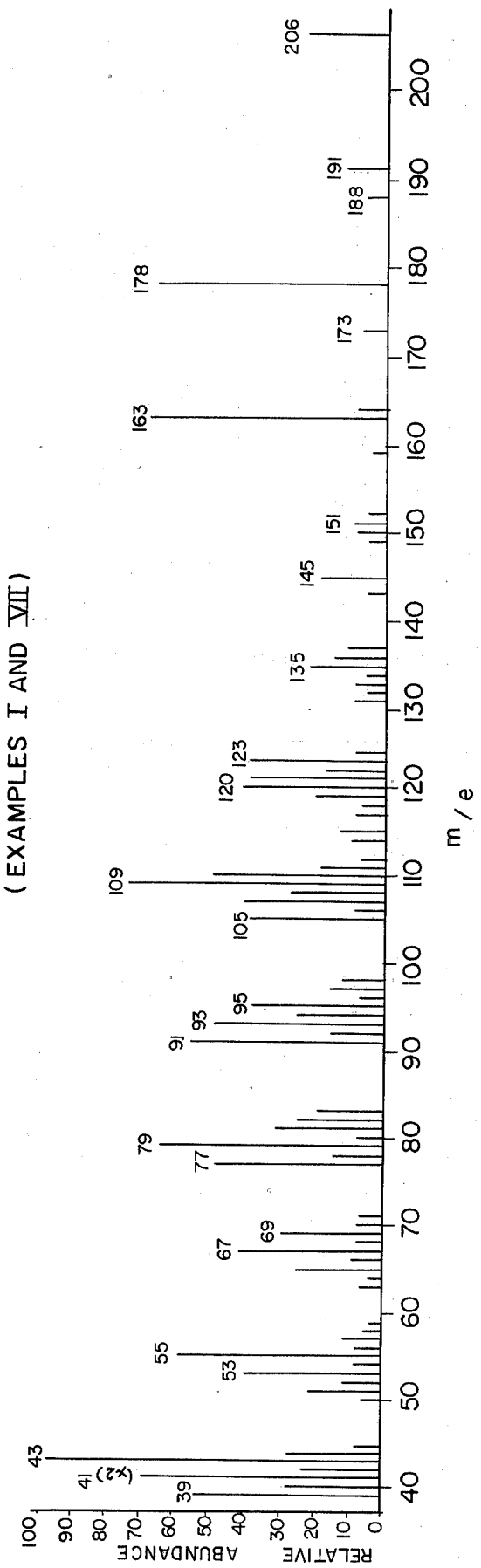

FIG.1 Mass Spectrum (EXAMPLES I AND VII)

NMR Spectrum
(EXAMPLES I AND VII)

Infrared Spectrum
(EXAMPLE I AND VII)

TETRACYCLIC ALCOHOLS

This application is a continuation-in-part of application for U.S. Letters Patent, Ser. No. 482,214, filed on June 24, 1974, now abandoned.

BACKGROUND OF THE INVENTION

Materials which can provide patchouli-like and woody fragrance notes are known in the art of perfumery. Many of the natural materials which provide such fragrances and contribute desired nuances to perfumery compositions are high in cost, vary in quality from one batch to another and/or are generally subject to the usual variations of natural products.

There is accordingly a continuing effort to find synthetic materials which will replace the essential fragrance notes provided by natural essential oils or compositions thereof. Unfortunately, many of these synthetic materials either have the desired nuances only to a relatively small degree or else contribute undesirable or unwanted odor to the compositions. The search for materials which can provide a more refined patchouli-like fragrance has been difficult and relatively costly in the areas of both natural products and synthetic products.

Buchi et al., 83 J. Am. Chem. Soc. 927 (1961), shows the production of a material called "patchoulione" which is stated to be octahydro-1,4,9,9-tetramethyl-3a,7-methanoazulen-5(4H)-one having the structure:

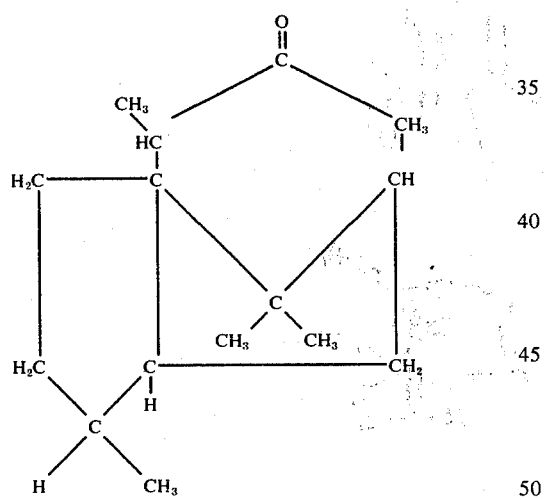

U.S. Pat. No. 3,748,284 issued on July 24, 1973 discloses perhydro derivatives of methanoazulene as having camphoraceous woody fragrances and having the ability to impart this fragrance to perfumed compositions and perfumed articles. The compounds disclosed are:

(a) Octahydro-1,4,9,9-tetramethyl-4,7-methanoazulen-3(2H)-one having the structure:

(b) Octahydro-1,4,9,9-tetramethyl-4,7-methanoazulen-2(3H)-one having the structure:

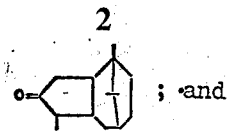

(c) Octahydro-1,4,9,9-tetramethyl-4,7-methanoazulen-8(7H)-one having the structure:

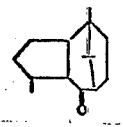

Umarani et al., Sept./Oct. 1969, P. & E.O.R., 307 discloses two compounds relevant to the instant case: "isopatchoulinol" having the structure:

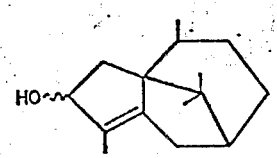

and "patchouli alcohol" having the structure:

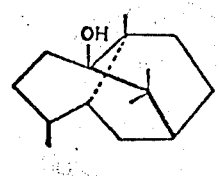

Mirrington and Schmalzl 37 *J. Org. Chem.* No. 18, 1972, pages 2871–2877 discloses the isolation of (−) patchouli alcohol having the structure:

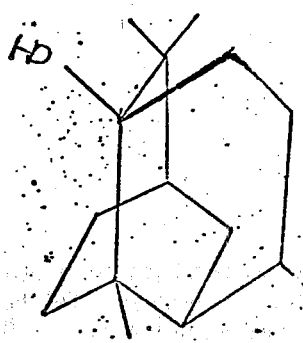

An article by Corey and Wipke entitled "Computer-Assisted Design of Complex Organic Syntheses" appearing in 166 Science 178 (1969) sets forth, interalia, the sequence of reactions leading to compounds having the structures:

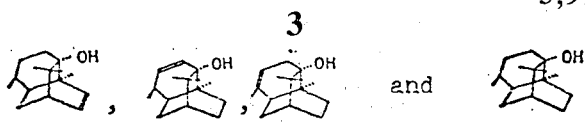 and 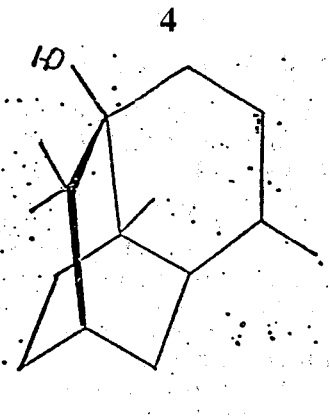

One of these reaction sequences involves performing the reactions:

(A)

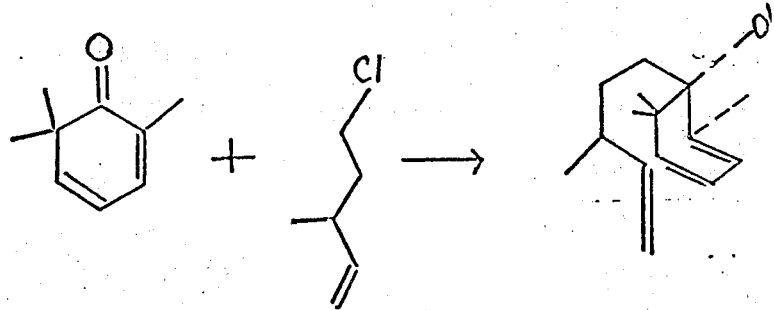

(B)

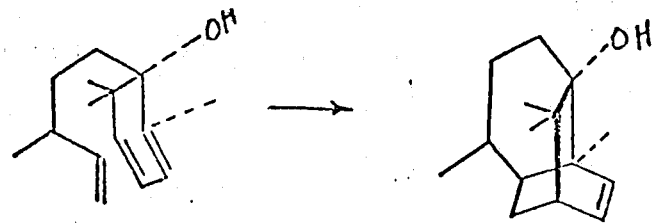

(C)

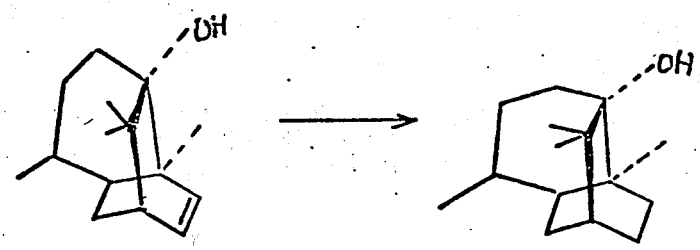

However, syntheses of methyl homologues and double compound isomers and an analogues patchouli alcohol and dihydropatchouli alcohol have not yet been disclosed in the prior art. Indeed, economic syntheses of patchouli alcohol itself do not appear to be given in the literature.

Danishevsky and Dumas 1968 Chemical Communication, Pages 1287–1288 discloses the synthesis of racemic patchouli alcohol and epi patchouli alcohol having the structure:

by means of cyclization of a compound having the structure:

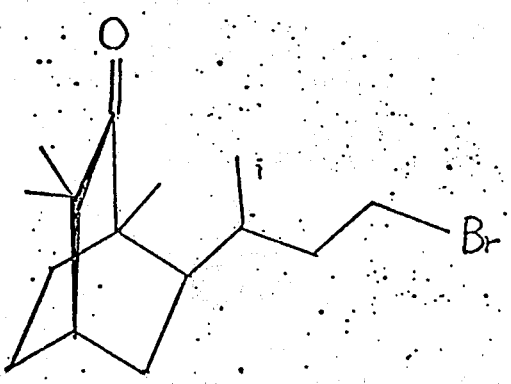

The use in perfumery of the compound having the structure:

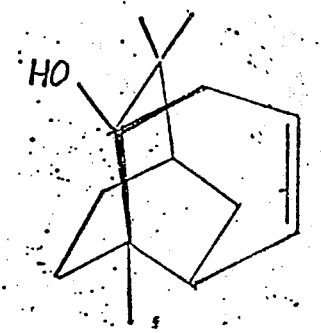

("norpatchoulinol") is disclosed in the following publications:
1. Belgian Patent No. 788,301 issued Mar. 1, 1973
2. German Offenlegungschrift 2,242,913 published Mar. 8, 1973
3. Dutch published Application 72/11760 published Mar. 5, 1973

A product of the reduction of this compound is also disclosed ("dihydro norpatchoulinol"). This product has the structure:

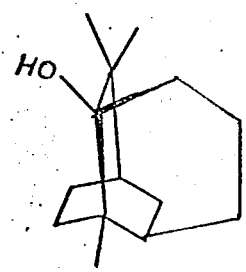

It is also disclosed in application for U.S. Pat. No. 436,846 filed on Jan. 28, 1974 that as a result of analyzing natural patchouli oil, it was found that cis-2-n-pentylcyclopropane-1-carboxylic acid having the structure:

is a key component for patchouli fragrance having a patchouli-like animal, leathery note and having the capability of imparting such notes to perfumes and cosmetic compositions.

Tetracyclic terpenes having structures and properties different in kind from the compounds of our invention have been previously examined and synthesized, for example, "ishwarane" and "ishwarone" having the structures:

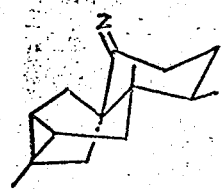

wherein Z=H, H or Z=O
as well as another tetracyclic ketone having the structure:

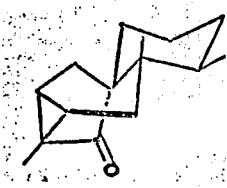

(Kelly et al., Can. J. Chem. 50 (21) 3455–65, 1972) and "myliol" having the structure:

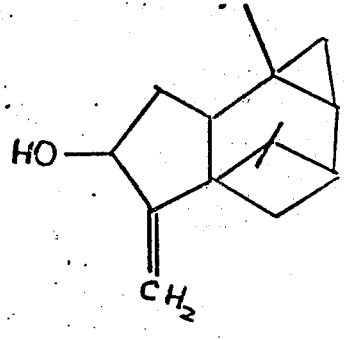

obtained from liverwort M. Taylorii (Benesova et al., Collect. Czech. Chem. Commun. 38 (4) 1084–90, 1973), Benesova et al. also discloses a compound having the structure:

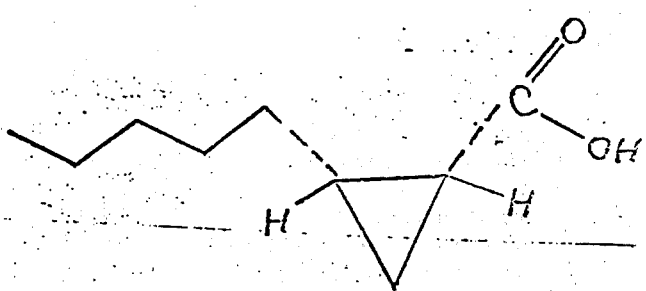

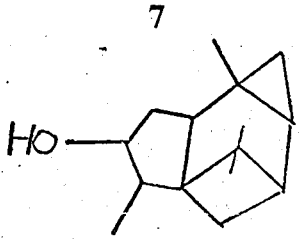

The compounds of our invention have properties considered to be unobvious, unexpected and advantageous with respect to the properties of the above mentioned prior art compounds.

THE INVENTION

It has now been determined that each of two particular tetracyclic alcohols are capable of imparting (or altering or modifying or enhancing) a patchouli fragrance to (or in) various consumable materials. Briefly, our invention contemplates altering, modifying, enhancing (or imparting) the fragrance of (or to) such consumable materials as perfumes, perfume formulations and perfumed articles by adding thereto a small but effective amount of at least one of the novel tetracyclic alcohols either in admixture with other organoleptically compatible and non-reactive chemical compounds or synthetic or natural oils or in substantially pure form, having one of the structures:

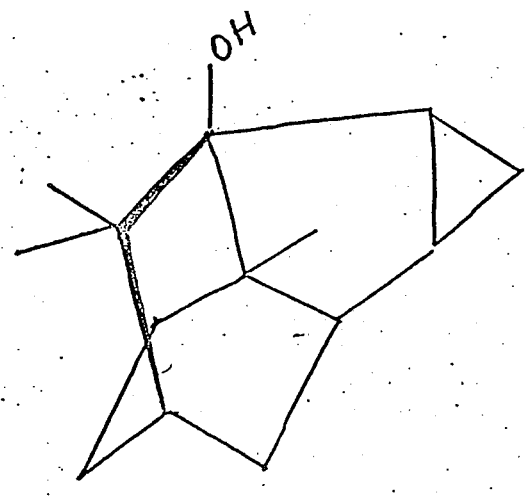

(I)

or

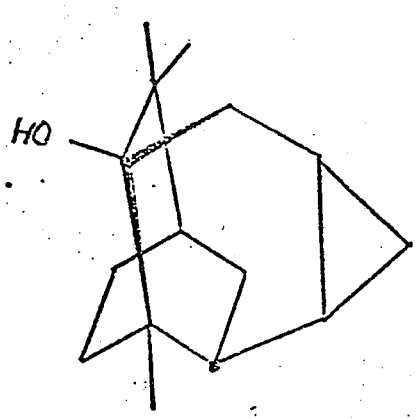

(II)

The above structures are intended to represent all of the stereoisomers of the compounds of our invention, to wit:

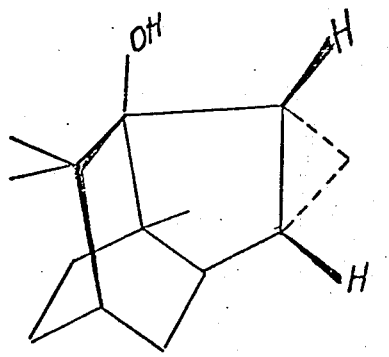

(Ia)

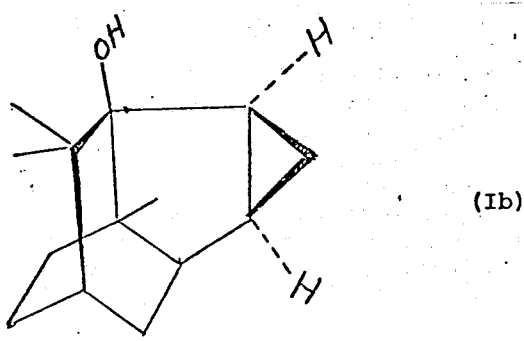

(Ib)

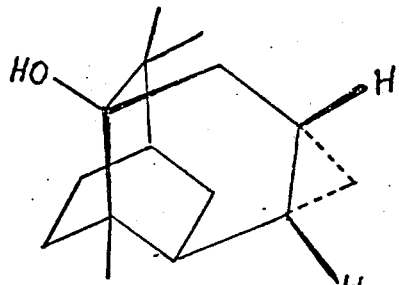

(IIa)

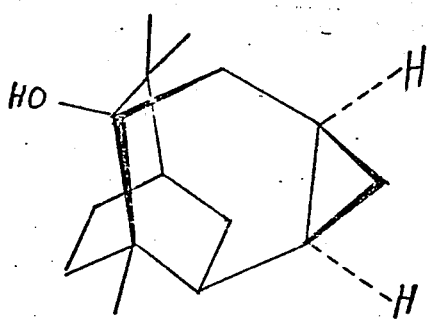

(IIb)

These stereoisomers individually, as well as in admixture are intended to be encompassed within the scope of our invention.

The novel compounds of our invention also include precursors for the foregoing compounds, and thus are defined by the generic structure:

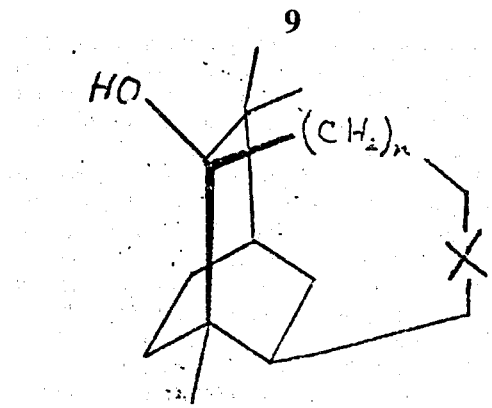

wherein n is 0 or 1 and X is selected from the group consisting of 1,2-cyclopropylene having the structure:

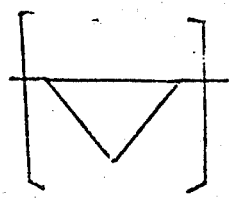

and 1,2-ethenylene having the structure:

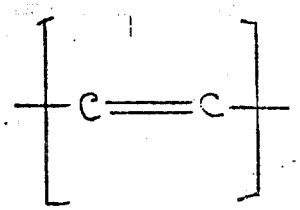

The tetracyclic alcohols produced according to the processes of our invention, may be racemic mixtures or individual stereoisomers, such as is the case concerning an isomer of patchouli alcohol which is obtained from patchouli oil.

The tetracyclic alcohol having the structure:

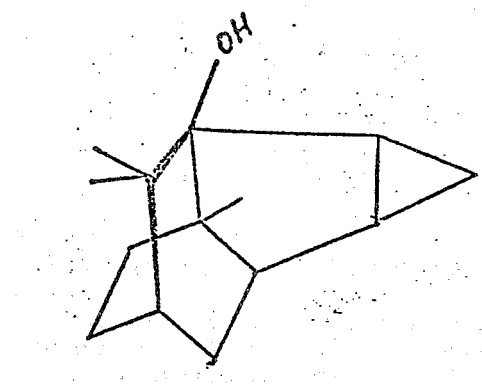

prepared according to the present invention can be obtained by means of the reaction sequence as set forth below:

a. First intimately admixing 2,6,6-trimethyl-cyclohexadien-1-one having the structure:

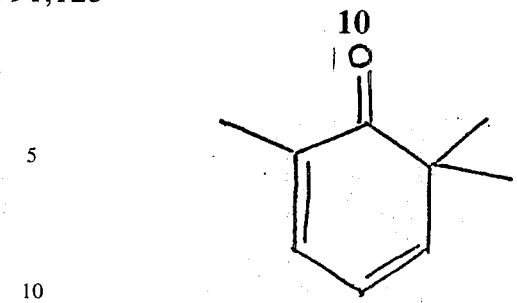

with an propargyl alcohol having the structure:

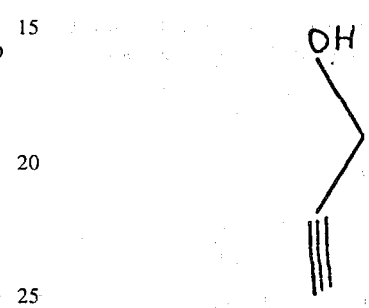

thereby forming a diene compound having the structure:

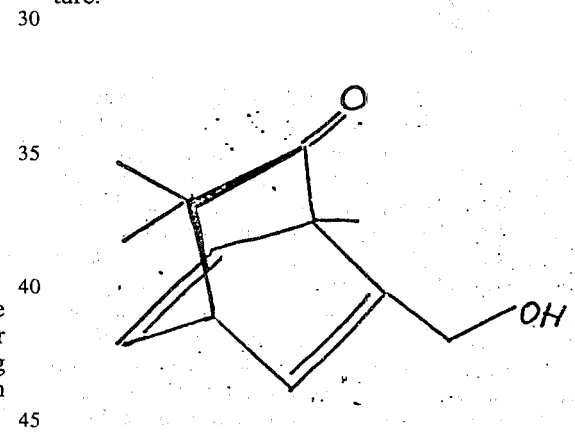

In this reaction, it is best to proceed at a temperature in the range of 200°–260° C with the most preferred temperature being 220° C. The reaction may be carried out in the presence of an inert solvent such as benzene, hexane or cyclohexane (or any other inert solvent) or the reaction may be carried out in the absence of solvent. Although, either the acetylenic compound or the cyclohexadienone may be used in excess, it is preferred to use equimolar quantities of each reactant.

The above-mentioned diene compound is then hydrogenated with hydrogen in the presence of a catalyst such as palladium, platinum, nickel or other suitable hydrogenation catalyst.

The reaction temperature may be from 20°–220° C with a temperature range of 100°–200° C being preferred. The reaction is preferably carried out at superatmospheric pressures and pressures in the range of 1–150 atmospheres are suitable. Preferred pressures range from 5–150 atmospheres.

The hydrogenation reaction gives rise to a ketone-carbinol product having the structure:

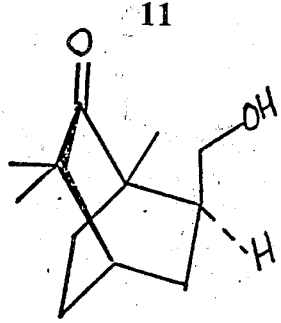

The next step involves conversion of the ketone-carbinol to a ketone carboxaldehyde having the structure:

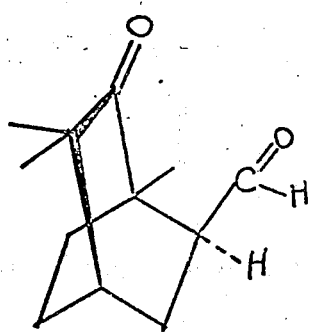

The oxidation of the ketone-carbinol to the ketone carboxaldehyde is most preferably carried out using a chromic acid oxidizing agent. Other oxidizing agents which may be used in the reaction in place of chromic acid are potassium permanganate, manganese dioxide, oxygen and air. It is most preferable to carry out this second oxidation reaction in the presence of a solvent such as pyridine although other solvents are also useful, such as alpha-picoline, beta-picoline, delta-picoline, piperidine and ethanol amine. The next step of the reaction sequence of the process of our invention involves the chloro-methylenation of the ketone-carboxaldehyde to form a ketone-chlorovinyl compound having the name, 1,3,3-trimethyl-6-(2-chloroethenyl) bicyclo-(2.2.2)-octan-2-one, and the structure:

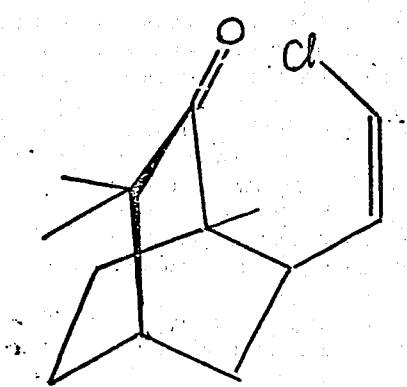

Such chloro-methylenation is carried out by reacting the 1,3,3-trimethyl-bicyclo-(2.2.2)-octan-2-one-6-carboxaldehyde with a chloro-methylenating agent which will form a "cis" chlorovinyl compound, at least in major proportion (so that the subsequent cyclization may be effected) preferably triphenylphosphine chloromethylene, at reflux conditions. Preferably, the chloro-methylenating reagent is in excess with respect to the ketone-carboxaldehyde reactant. At the end of the reaction, the excess volatile chloro-methylenating agent is destroyed by reaction with water and the resulting ketone-chlorovinyl compound is rush distilled and used without further purification in the next step of this sequence, the cyclization reaction. Only the "cis" chlorovinyl compound is desired to be produced as this isomer, as opposed to the "trans" isomer, is the one that can be cyclized in the next step of the process sequence of our invention.

The ketone-chlorovinyl compound thus produced is then cyclized by treating same with an alkali metal selected from the group consisting of sodium, potassium or lithium. The cyclization may be carried out in diethyl ether, tetrahydrofuran or benzene. The reaction temperature preferred is the reflux temperature of the reaction mass at atmospheric pressure and is a function of the solvent used. Thus, for example, when using tetrahydrofuran solvent, the cyclization reaction temperature is approximately 65° C. The reaction can be carried out at temperatures ranging from 0° up to 100° C. For the cyclization, the mole ratio of ketone to metal is preferably 7:1 although mole ratio of ketone to metal is from 1:1 up to 10:1 may be used. The product of this cyclization, unsaturated tetracyclic alcohol, has the structure:

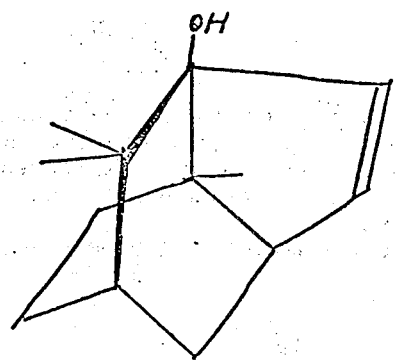

and the name, 9,10,10-trimethyl-tricyclo(4.3.1.0$^{4,9}$) dec-2-en-1-ol.

If desired, prior to the next reaction, when the cyclization reaction is completed, the reaction mixture may "worked-up" using routine purification procedures including the unit operations of extraction, and/or distillation.

The next step of the reaction sequence of our invention involves the replacement of the double bond with a cyclopropylene moiety to form the tetracyclic alcohol of our invention having the structure:

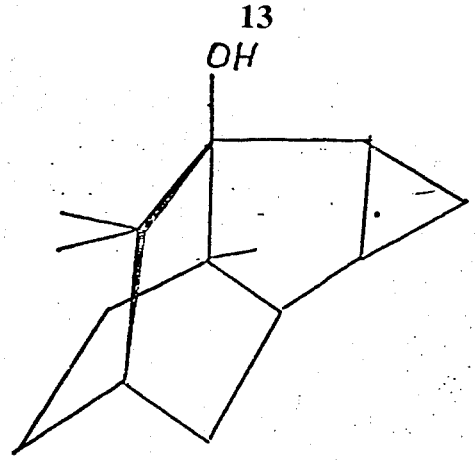

This synthesis is carried out using an excess of diiodomethane with respect to the unsaturated tetracyclic alcohol. The reaction is most preferably carried out in an inert solvent such as diethyl ether or cyclohexane. The reaction is carrie out preferably under reflux conditions at atmospheric pressure (thus, in the case of the use of diethyl ether as a solvent, the temperature of reaction is 36°–46° C). The reaction takes place in the presence of a zinc-copper couple prepared by admixing the zinc dust, cuprous chloride powder and the solvent used in the reaction.

When the cyclopropylenation reaction is complete, the reaction mixture is "worked-up" using routine purification procedures including the unit operations of extraction, crystallization, preparative chromatographic techniques, drying and/or distillation.

The resulting compound may be, if desired, thus isolated in a substantially pure state.

The compound (II) of our invention, having the structure:

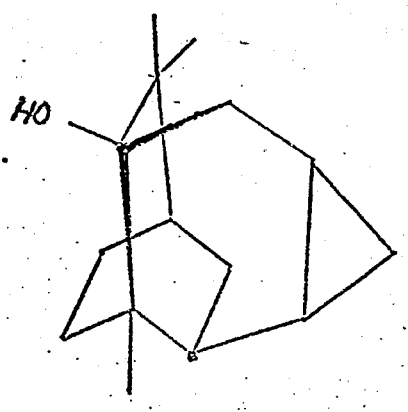

is prepared by means of replacement of the double bond of norpatchoulinol having the structure:

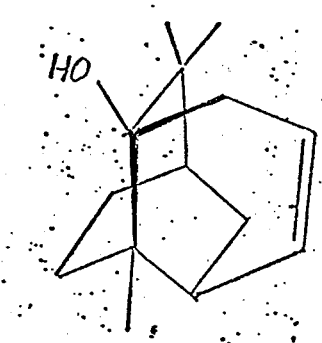

with a cyclopropylene moiety.

This synthesis is carried out using an excess of diiodomethane with respect to the unsaturated tetracyclic alcohol. The reaction is most preferably carried out in an inert solvent such as diethyl ether or cyclohexane. The reaction is carried out preferably under reflux conditions at atmospheric pressure (this, in the case of the use of diethyl ether as a solvent, the temperature of reaction is 36°–46° C). The reaction takes place in the presence of a zinc-copper couple prepared by admixing the zinc dust, cuprous chloride powder and the solvent used in the reaction.

When the cyclopropylenation reaction is complete, the reaction mixture is "worked-up" using routine purification procedures including the unit operations of extractions, crystallization, preparative chromatographic techniques, drying and/or distillation.

The resulting compound may, if desired, thus isolated in a substantially pure state.

The tetracyclic alcohols of our invention having a patchouli aroma with warm, sweet, woody and camphoraceous notes, can be used to contribute, modify, alter or enhance warm, patchouli-like aromas.

Although existant in relatively low proportions in patchouli oil, compound (I) of our invention is considered to be at least one of the primary "patchouli" aroma contributors of all of the constituents of patchouli oil. Indeed, the relative strength of its aroma is several-fold that of any other known aroma contributors heretofore found in patchouli oil; and this property is unexpected.

It will be appreciated from the present disclosure that the tetracyclic alcohols and mixtures thereof according to the present invention can be used to alter, vary, fortify, modify, enhance or otherwise improve the aroma of a wide variety of consumable materials, e.g. perfumes, perfumed articles and colognes which are organoleptically sensed.

The terms "alter" and "modify" in their various forms will be understood herein to mean the supplying or imparting of an aroma character of note to an otherwise bland, relatively odorless substance, or augmenting an existing aroma characteristic where the natural aroma is deficient in some regard; or supplementing the existing aroma impression to modify the organoleptic character thereof.

The term "enhance" in its various forms is used herein to mean the intensification of an aroma characteristic or note without the modification of the quality thereof. Thus, "enhancement" of an aroma, means that the enhancement agent does not add any additional aroma nuance.

As olfactory agents the tetracyclic alcohols of this invention can be formulated into or used as components of a "perfume composition".

The term "perfume composition" is used herein to mean a mixture of organic compounds, including, for example, alcohols, aldehydes, ketones, nitriles, esters, and frequently hydrocarbons which are admixed so that the combined odors of the individual components produce a pleasant or desired fragrance. Such perfume compositions usually contain: (a) the main note of the "bouquet" or foundation-stone of the composition; (b) modifiers which round-off and accompany the main note; (c) fixatives which include odorous substances which lend a particular note to the perfume throughout all stages of evaporation, and substances which retard evaporation; and (d) top-notes which are usually low-boiling fresh smelling materials.

In perfume compositions the individual component will contribute its particular olfactory characteristics, but the overall effect of the perfume composition will be the sum of the effect of each ingredient. Thus, the tetracyclic alcohols of this invention, can be used to alter the aroma characteristics of a perfume composition, for example, by highlighting or moderating the olfactory reaction contributed by another ingredient in the composition.

The amount of the tetracyclic alcohols of this invention which will be effective in perfume compositions depends on many factos, including the other ingredients, their amounts and the effects which are desired. It has been found that perfume compositions containing as little as 2 percent of the tetracyclic alcohols of this invention, or even less, can be used to impart a patchouli scent to soaps, cosmetics, and the other products. The amount employed can range up to 50% or higher and will depend on considerations of cost, nature of the end product, the effect desired on the finished product and particular fragrance sought.

The tetracyclic alcohols of this invention can be used alone or in a perfume composition as an olfactory component in detergents and soaps, space odorants and deodorants; perfumes; colognes; toilet waters; bath salts; their preparations such as lacquers, brilliantines, pomades, and shampoos; cosmetic preparations such as creams, deodorants, hand lotions, and sun screens; powders such as talcs, dusting powders, face powder, and the like.

Detergents, soaps, space deodorants, odorants, toilet waters, bath salts, hair preparations, cosmetic preparations and powders are grouped within the genus, "perfumed article".

When used as an olfactory component of a perfumed article, as little as 0.01 percent of the tetracyclic alcohols will suffice to impart a warm patchouli aroma. Generally, no more than 0.5 percent is required.

In addition, the perfume composition can contain a vehicle or carrier for the tetracyclic compounds alone or with other ingredients. The vehicle can be a liquid such as an alcohol such as ethanol, a glycol such as propylene glycol, or the like. The carrier can be an absorbent solid such as a gum or components for encapsulating the composition.

The following examples are given to illustrate embodiments of the invention as it is presently preferred to practice it. It will be understood that these examples are illustrative, and the invention is not to be considered as restricted thereto except as indicated in the appended claims. It is to be understood that unless otherwise stated all parts, proportions and percentages are by weight.

EXAMPLE I

ISOLATION OF 10,11,11-TRIMETHYL-TETRACYCLO(5.3.1.0$^{2,4}$.0$^{5,10}$)UNDECAN-1-OL FROM PATCHOULI OIL 250 g patchouli oil is chromatographed in a column consisting of 2.5 kg 5% deactivated silicic acid (95% silicic acid and 5% deionized water). The column is first eluted with 3 liters of isopentane, yielding a "hydrocarbon fraction" weighing 147 g after solvent evaporation. The column is then eluted with 4 liters of diethyl ether, yielding 108 g of an "oxygenated material fraction" after evaporation of the diethyl ether from the eluate. 90.5 g of the said "oxygenated material fraction" is distilled on a spinning band column yielding 38 fractions. Fractions 12 and 13 (weighing 1.8 g) distill at 58° C and 0.1 mm Hg pressure. 1.6 g of this distillate are dissolved in 10 cc of isopentane, and the resulting isopentane solution is chromatographed on a column consisting of 40 g of 5% deactivated silicic acid (95% silicic acid and 5% deionized water). The column is then eluted as follows:

| Eluting Solvent | Solute Contents of Eluate |
|---|---|
| Isopentane | 0 |
| 1% diethyl ether in isopentane | 0 |
| 2% diethyl ether in isopentane-Forty-nine fractions each containing 20 ml solution | 49th fraction is solution containing desired product and other products |

After evaporation of the solvent, the solute is chromatographed on a GLC column under the following conditions:

| Dimensions: | 22' × 0.125", 5% Carbowax 20M; |
|---|---|
| Programmed at: | 100 240° C at 2° C/minute; |
| Chart Speed: | 2 inches/min. |

The major peak is trapped ten times in succession using the GLC column with the foregoing conditions. The major peak is then rechromatographed on a second GLC column under the following conditions:

| Dimensions: | 22' × 0.125", 5% SE-30 (A methyl silicone oil available from Analabs, Inc. of P.O. Box 501, North Haven, Conn. 06473) |
|---|---|
| Programmed at: | 100 240° C at 2° C/minute; |
| Chart Speed: | 2 inches/minute |

Two peaks now result, a major peak which is patchouli alcohol and a minor peak (collected as a white crystalline solid) having a powerful patchouli odor with warm, woody, sweet and camphoraceous notes. The minor peak represents a substantially pure compound having the structure:

17

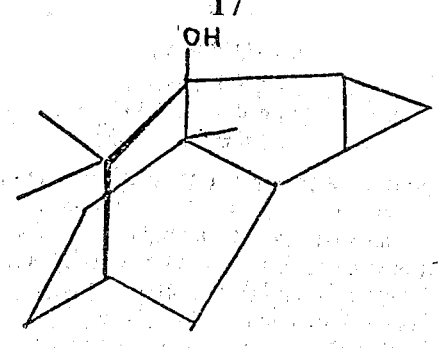

as confirmed by mass spectral analysis, infra-red analysis and nuclear magnetic resonance analysis:

Mass Spectral Analysis:
Parent peak, then in decreasing intensity:
206, 43, 109, 163, 178, 79, 55, 91
The mass spectrum is illustrated in FIG. 1.
NMR Analysis (CDCl$_3$):

| Signal | Interpretation |
|---|---|
| 0.63 (broad, 1H) 0.78 (broad, 3H) | H\\\_/H  /X\  H/  \H |
| 0.92 s, 3H 0.97 s, 3H 1.02 s, 3H | Three CH$_3$ groups |
| 1.1–2.3 (m, 2H) | —CH$_2$— groups |

Figure 2:
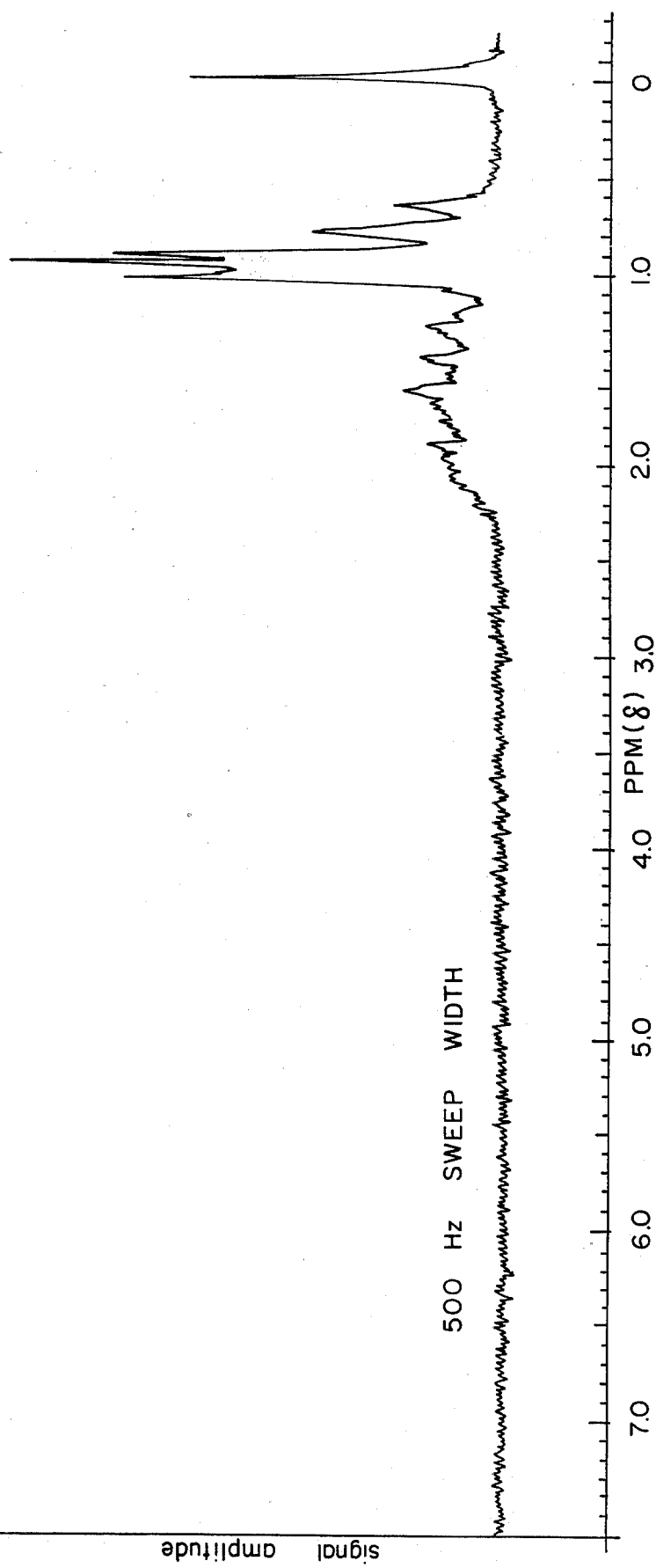

The NMR spectrum is illustrated in FIG. 2.
Infra-red Analysis (CCl$_4$ solution):

| Peak | Interpretation |
|---|---|
| 3600 cm$^{-1}$ | —OH group |

Figure 3:
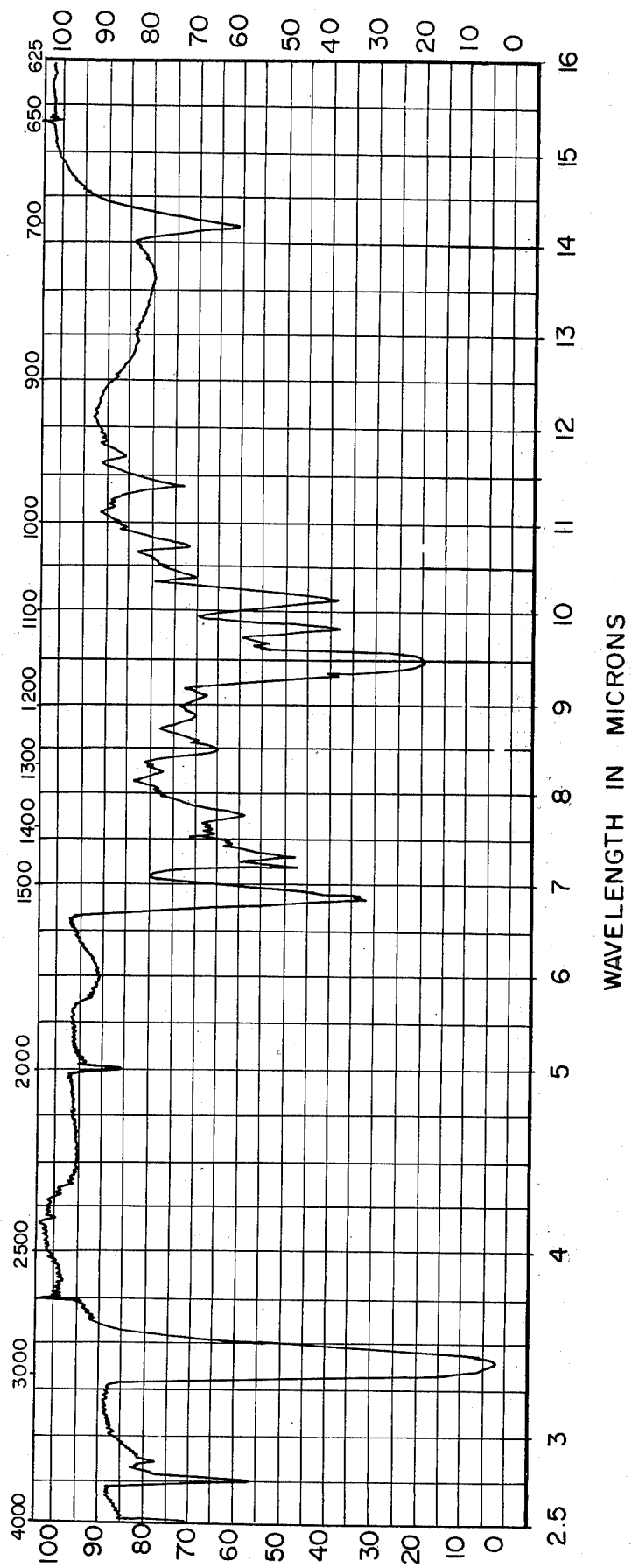

The infra-red spectrum is illustrated in FIG. 3.

EXAMPLE II

PREPARATION OF 1,3,3-TRIMETHYL-6-HYDROXYMETHYL-BICYCLO-(2.2.2)-OCTA-5,7-DIEN-2-ONE

A solution of 27.2 g (0.20 moles) of 2,6,6-trimethyl-cyclohexadien-1-one and 28 g (0.5 moles) of 3-propyn-1-ol (propargyl alcohol) in 300 cc of benzene is placed in a 2 liter stirred autoclave and heated to 220° C for 5 hours. At the end of this time, GLC shows no trimethylcyclohexadien-1-one remaining and the solvent is removed under vacuum and the residue is distilled to yield about 30 g of the product, 1,3,3-trimethyl-3-hydroxymethyl-bicyclo-(2.2.2)-octa-5,7-dien-2-one.

EXAMPLE III

PREPARATION OF 1,3,3-TRIMETHYL-6-HYDROXYMETHYL-BICYCLO-(2.2.2)-OCTAN-2-ONE

A mixture of 30 g of 1,3,3-trimethyl-6-hydroxymethyl-bicyclo-(2.2.2)-octa-5,7-dien-2-one, 0.5 g of 5% of palladium-carbon and 300 ml of isopropyl alcohol is added to a stirred autoclave. The autoclave is pressurized to 400 pounds per square inch with hydrogen and heated to 100° C for 6 hours. At the end of this time, the mixture is filtered, stripped of solvent and vacuum distilled, yielding about 27 g (90%) of the product, 1,3,3-trimethyl-6-hydroxymethyl-bicyclo-(2.2.2)-octan-2-one, having the structure:

18

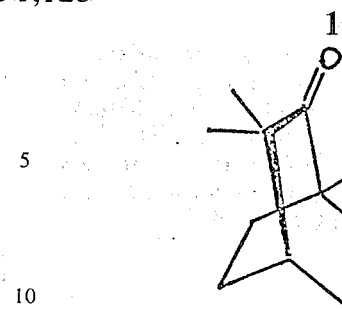

EXAMPLE IV

OXIDATION OF 1,3,3-TRIMETHYL-6-HYDROXYMETHYL-BICYCLO-(2.2.2)-OCTAN-2-ONE TO 1,3,3-TRIMETHYL BICYCLO-(2.2.2)-OCTAN-2-ONE-6-CARBOXALDEHYDE

Chromium trioxide (25 g) is dissolved in 25 ml of water. The aqueous chromic acid solution is then added slowly to pyridine (250) ml cooled to 5° C. 20 g of 1,3,3-trimethyl-6-hydroxymethyl-bicyclo-(2.2.2)-octan-2-one is then added dropwise to the solution at 0°–5° C with stirring in 5 minutes. The reaction is allowed to warm to room temperature (22° C) and is stirred overnight. The reaction mass is worked up by pouring into 500 ml of water and then removing any remaining solids by filtration. The aqueous mixture is extracted with 250 ml of ether and twice more with 75 ml portions of ether. The ether extracts are bulked and washed twice with equal volumes of water and once with 5% hydrochloric acid to remove any remaining pyridine. One final wash with water is carried out and the ether solution is dried over magnesium sulfate. Stripping the ether under house vacuum gives 11 g of residue. An IR run on the Perkin-Elmer 237 shows the product to be mostly aldehyde. GLC analysis (20 feet × ¼ inch 5% Carbowax column, programmed 100°–200° C at 4°/min.) shows one major product. The crude aldehyde having the structure set forth below is not purified nor submitted for spectral data but is immediately reacted with triphenylphosphine chloromethylene.

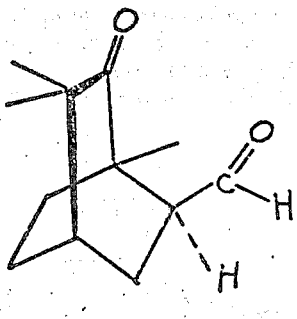

EXAMPLE V

PREPARATION OF 1,3,3-TRIMETHYL-6-(2-CHLOROVINYL)-BICYCLO-(2.2.2)-OCTAN-2-ONE

A mixture of 30 g of triphenylphosphine, 200 ml of anhydrous ether and 11 g of methylene chloride is cooled to −30° and 77 ml of 1.3M n-butyl lithium solution is added over one hour. To the stirred solution is added 11 g of crude 1,3,3-trimethyl-bicyclo-(2.2.2)-octan-2-one-6-carboxaldehyde. The mixture is slowly heated to reflux and held at reflux for 2 hours. The mixture is poured into 100 ml of water and the organic layer is separated and dried over Mg 80₄ and the solvent is stripped off the product. Structure:

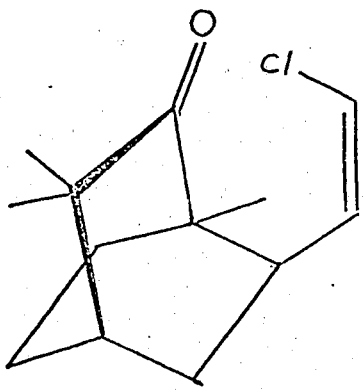

is obtained by vacuum distillation and is a mixture of the cis and trans material. The crude distillate is used in the following reaction.

EXAMPLE VI

PREPARATION OF 9,10,10-TRIMETHYL-TRICYCLO-(4.3.1.0$^{4,9}$) DEC-2-EN-1-OL

A sodium sand is prepared by heating 11.5 g of sodium in xylene and stirring. The xylene is decanted and replaced by 300 cc of anhydrous tetrahydrofuran. A solution of 8 g of 1,3,3-trimethyl-6-(2-chlorovinyl)-bicyclo-(2.2.2)-octan-2-one in 50 cc of tetrahydrofuran is added with stirring at room temperature over a 15 minute period. A slight exotherm occurs during addition. The solution is brought to reflux and held there for 3 hours. At the end of this time, the solution is decanted from the excess sodium and is acidified with 5% HCl. The excess acid is neutralized by a single wash with saturated sodium bicarbonate solution. The solution is dried over magnesium sulfate, filtered and stripped, yielding a residue which is recrystallized from hexane to yield about 6 g of the title product having the structure:

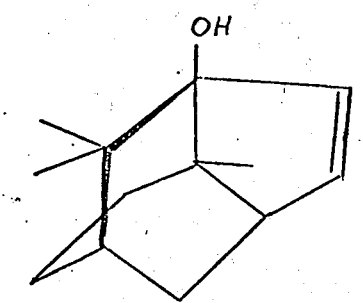

confirmed by MS, NMR and IR analyses.

EXAMPLE VII

PREPARATION OF 10,11,11-TRIMETHYL-TETRACYCLO-(5.3.1.-0$^{2,4}$.0$^{5,10}$) UNDECAN-1-OL

A suspension of 19 g of zinc dust and 29 g of cuprous chloride powder in 125 ml of ether are stirred under reflux for thirty minutes. Diiodomethane (14.8 ml) is added dropwise over a twenty minute period. No external heat is required and the addition is carried out at a rate sufficient to maintain reflux (36°–41° C). 1.5 g of the product produced in Example VI, 9,10,10-trimethyl-tricyclo-(4.3.1.0$^{4,9}$)-dec-2-en-1-ol, is then added dropwise over a twenty minute period without external heating. Reflux is maintained (41°–46° C) throughout addition of the dec-2-en-1-ol. The reaction mass is refluxed daily for 8.5 hours for 5 days (42 hours in all) adding more ether and diiodomethane as required. The course of the reaction is followed by GLC (20 feet × ¼ inch 5% SE-30 prog. 100°–220° C at [4°/min.).

After the last reflux the mixture is allowed to cool to room temperature overnight and then filtered. The filtrate is poured into an equal volume of water and the ether layer is separated and washed once with 50 ml of 10% sodium thiosulfate and then twixe with 100 ml portions of water. The ether layer is dried over magnesium sulfate. The filtered ether solution is stripped under house vacuum to 40° C and the residue (1 g) is recrystallized from hexane, yielding about 0.25 g of the title material. GLC analysis of the solid shows the mixture to be 98% product and 2% starting material. (GLC conditions: 20 feet × ¼ inch 5% Carbowax 20M column, programmed 100°–200° C at 4°/min.). The structure of the product is:

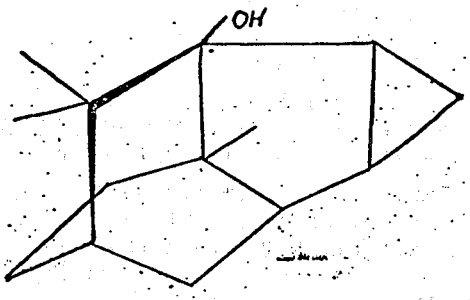

as confirmed by mass spectral, NMR and IR analyses, identical to that of the product of Example I, and is as follows:

Mass Spectral Analysis:
  Parent peak, then in decreasing intensity:
  206, 43, 109, 163, 178, 79, 55, 91
The mass spectrum is illustrated in FIG. 1.
NMR Analysis (CDCl₃):

| Signal | Interpretation |
|---|---|
| 0.63 (broad, 1H) | 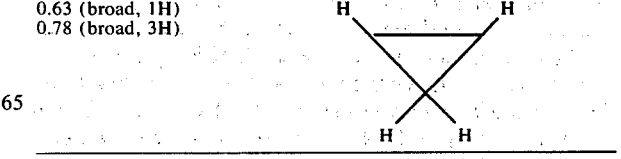 |
| 0.78 (broad, 3H) | |
| 0.92 s, 3H | |
| 0.97 s, 3H | |

-continued

| | |
|---|---|
| 1.02 s, 3H | Three CH$_3$ groups |
| 1.1–2.3 (m,2H) | —CH$_2$—groups |

The NMR spectrum is illustrated in FIG. 2.
Infra-red Analysis (CCl$_4$ solution):

| Peak | Interpretation |
|---|---|
| 3600 cm$^{-1}$ | —OH group |

The infra-red spectrum is illustrated in FIG. 3.

EXAMPLE VIII

PERFUME FORMULATION

The following patchouli cologne perfume formulation is prepared:

| Ingredients | Parts by Weight |
|---|---|
| Bergamot oil | 200 |
| Orange Oil Florida | 300 |
| Mandarin oil | 50 |
| Lemon oil | 70 |
| Neroli | 10 |
| 4-(4-methyl-4-hydroxyamyl) Δ$^3$-cyclohexene carboxaldehyde | 30 |
| Ylang Extra | 2 |
| Gamma methyl ionone | 5 |
| 3a-methyl-dodecahydro-6,6,9a-trimethylnaphtho-(2.1-b) furan | 3 |
| Shiff base of methylanthranilate and hydroxycitronellal (methyl-n-3,7-dimethyl-7-hydroxyoctylidene anthranilate) | 5 |
| 1',2',3',4',5',6',7',8'-octahydro-2',3',8',8'-tetramethyl-2'-acetonaphthone isomer mixture prepared according to the process of Example VII of application for U.S. Letters Patent No. 434,948 filed on January 21, 1974 | 10 |
| 10,11,11-trimethyl-tetracyclo-(5.3.1.0$^{2,4}$.0$^{5,10}$) undecan-1-ol produced according to the process of Example VII | 15 |

10,11,11-trimethyl-tetracyclo-(5.3.1.0$^{2,4}$.0$^{5,10}$) undecan-1-ol imparts a warm patchouli-like character to this "patchouli cologne" compositon.

EXAMPLE IX

PREPARATION OF A SOAP COMPOSITION

A total of 100 g of soap chips produced from unperfumed sodium base toilet soap made from tallow and coconut oil are mixed with 1 g of the perfume composition set forth in Example VIII until a substantially homogeneous composition is obtained. The soap composition manifests a characteristic "patchouli cologne" aroma having a warm patchouli-like character.

EXAMPLE X

PREPARATION OF A SOAP COMPOSITION

A total of 100 g of soap chips produced from unperfumed sodium base toilet soap made from tallow and coconut oil is mixed with 1 g of 10,11,11-trimethyl-tetracyclo-(5.3.1.0$^{2,4}$.0$^{5,10}$) undecan-1-ol until a substantially homogeneous composition is obtained.

The soap composition manifests a warm patchouli character with warm, woody, sweet and camphoraceous notes.

EXAMPLE XI

PREPARATION OF A DETERGENT COMPOSITION

A total of 100 g of a detergent powder sold under the trademark "RINSO" are mixed with 0.15 g of a perfume composition containing the mixture obtained in Example VIII until a substantially homogeneous composition having a "patchouli cologne" fragrance with a warm patchouli-like character is obtained.

EXAMPLE XII

PREPARATION OF A COSMETIC BASE

A cosmetic powder is prepared by mixing 100 g of talcum powder with 0.25 g of the perfume composition of Example VIII in a ball mill. A second cosmetic powder is similarly prepared except that the mixture produced in Example VIII is replaced with the product produced in Example VII, 10,11,11-trimethyl-tetracyclo-(5.3.1.0$^{2,4}$.0$^{5,10}$) undecan-1-ol. The cosmetic powder containing the material of Example VIII has a "patchouli cologne" fragrance with a warm patchouli-like character. The cosmetic powder produced using this material of Example VII has a patchouli aroma with warm, woody, sweet and camphoraceous notes.

EXAMPLE XIII

LIQUID DETERGENT CONTAINING 10,11,11-TRIMETHYL-TETRACYCLO-(5.3.1.0$^{2,4}$.0$^{5,10}$) UNDECAN-1-OL

Concentrated liquid detergents with a patchouli-like odor containing 0.2%, 0.5% and 1.2% of the product produced in accordance with the process of Example VII, 10,11,11-trimethyl-tetracyclo-(5.3.1.0$^{2,4}$.0$^{5,10}$)-undecan-1-ol, are prepared by adding the appropriate quantity of 10,11,11-trimethyl-tetracyclo-(5.3.1.0$^{2,4}$.0$^{5,10}$)-undecan-1-ol to the liquid detergent known as P-87. The patchouli aroma of the liquid detergent increases with increasing concentration of the 10,11,11-trimethyl-tetracyclo-(5.3.1.0$^{2,4}$.0$^{5,10}$)-undecan-1-ol of this invention.

EXAMPLE XIV

PREPARATION OF COLOGNE AND HANDKERCHIEF PERFUME

The composition of Example VIII is incorporated in a cologne having a concentration of 2.5% in 85% aqueous ethanol; and into a handkerchief perfume in a concentration of 20% (in 95% ethanol). The use of the composition of Example VIII affords a distinct and definite "patchouli cologne" aroma having a warm patchouli-like character to the handkerchief perfume and to the cologne.

EXAMPLE XV

COLOGNE AND HANDKERCHIEF PERFUME

The 10,11,11-trimethyl-tetracyclo-(5.3.1.0$^{2,4}$.0$^{5,10}$) undecan-1-1 produced by the process of Example VII is incorporated into a cologne having a concentration of 2.5% in 85% ethanol; and into a handkerchief perfume in a concentration of 10% (in 95% ethanol). The 10,11-11-trimethyl-tetracyclo-(5.3.1.0$^{2,4}$.0$^{5,10}$) undecan-1-ol produced in Example VII affords a distinct and definite patchouli aroma with warm, woody, sweet and camphoraceous notes to be handkerchief perfume and to the cologne.

EXAMPLE XVI

PREPARATION OF 11,12,12-TRIMETHYL-TETRACYCLO-(6,3.1.0$^{3,5}$.0$^{6,11}$) DODECAN-1-OL

A suspension of 19 g of zinc dust and 30 g of cuprous chloride powder in 125 ml of ether are stirred under reflux for 30 minutes. Diiodomethane (16 ml) is added dropwise over a 20 minute period. No external heat is required and the addition is carried out at a rate sufficient to maintain reflux (36°–41° C).

Norpatchoulinol is then added dropwise over a 20 minute period without external heating. Reflux is maintained (42°–46° C) throughout the addition of dehydronorpatchoulinol. The reaction mass is refluxed daily for 8.5 hours for five days (42 hours in all) adding more ether and diiodomethane as required. The course of the reaction is followed by GLC (20 feet × ¼ inch 5% SE-30 prog. 100°–220° at 4°/min.)

After the last reflux the mixture is allowed to cool to room temperature overnight and then filtered. The filtrate is poured into an equal volume of water and the ether layer is separated and washed once with 50 ml of 10% sodium thiosulfate and then twice with 100 ml portions of water. The ether layer is dried over magnesium sulfate. The filtered ether solution is stripped under house vacuum to 40° C and the residue (1.1 g) is recrystallized from hexane: yield, 0.35 g of the title compound. GLC analysis of the solid shows the mixture to be 95% product and 5% starting material. (GLC conditions: 20 feet .× ¼ inch 5% Carbowax 20M column, programmed 100°–200° C at 4°/min.). The structure of the product is

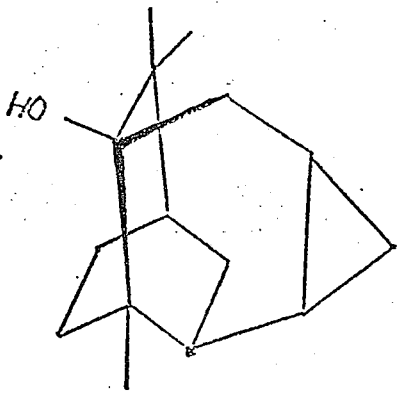

as confirmed by mass spectral, NMR and IR analyses.

EXAMPLE XVII

PERFUME FORMULATION

The following "patchouli cologne" perfume formulation is prepared:

| Ingredients | Parts by Weight |
| --- | --- |
| Bergamot oil | 200 |
| Orange Oil Florida | 300 |
| Mandarin oil | 50 |
| Lemon oil | 70 |
| Neroli | 10 |
| 4-(4-methyl-4-hydroxyamyl) Δ$^3$-cyclohexene carboxaldehyde | 30 |
| Ylang Extra | 2 |
| Gamma methyl ionone | 5 |
| 3a-Methyl-dodecahydro-6,6,9a-trimethylnaphtho-(2,1-b) furan | 3 |
| Shiff base of methylanthranilate and hydroxycitronellal (methyl-n- | 5 |

EXAMPLE XVII-continued

PERFUME FORMULATION

The following "patchouli cologne" perfume formulation is prepared:

| Ingredients | Parts by Weight |
| --- | --- |
| 3,7-dimethyl-7-hydroxyoctylidene anthranilate) | |
| 1',2',3',4',5',6',7',8'-octahydro-2',3',8',8'-tetramethyl-2'-aceto-naphthone isomer mixture prepared according to the process of Example VII of application for U.S. Letters Patent No. 434,948 filed on January 21, 1974 | 10 |
| 11,12,12-Trimethyl-tetracyclo-(6.3.1.0$^{3,5}$.0$^{6,11}$) dodecan-1-ol produced according to the process of Example XVI | 15 |

11,12,12-trimethyl-tetracyclo-(6.3.1.0$^{3,5}$.0$^{6,11}$)-dodecan-1-ol imparts a warm patchouli-like character to this "patchouli cologne"

EXAMPLE XVIII

PREPARATION OF A SOAP COMPOSITION

A total of 100 g of soap chips produced from unperfumed sodium base toilet soap made from tallow and coconut oil are mixed with 1 g of the perfume composition set forth in Example XVII until a substantially homogeneous composition is obtained. The soap composition manifests a characteristic "patchouli cologne" aroma having a warm patchouli-like character.

EXAMPLE XIX

PREPARATION OF A SOAP COMPOSITION

A total of 100 g of soap chips produced from unperfumed sodium base toilet soap made from tallow and coconut oil is mixed with 1 g of 11,12,12-trimethyl-tetracyclo-(6.3.1.0$^{3,5}$.0$^{6,11}$) dodecan-1-ol until a substantially homogeneous composition is obtained. The soap composition manifests a patchouli character with warm, woody, sweet and camphoraceous notes.

EXAMPLE XX

PREPARATION OF A DETERGENT COMPOSITION

A total of 100 g of a detergent powder sold under the trademark "RINSO" are mixed with 0.15 g of a perfume composition containing the mixture obtained in Example XVI until a substantially homogeneous composition having a "patchouli cologne" fragrance with a warm patchouli-like character is obtained.

EXAMPLE XXI

PREPARATION OF A COSMETIC BASE

A cosmetic powder is prepared by mixing 100 g of talcum powder with 0.25 g of the perfume composition of Example VIII in a ball mill. A second cosmetic powder is similarly prepared except that the mixture produced in Example XVII is replaced with the product produced in Example XVI, 11,12,12-trimethyl-tetracyclo-(6.3.1.0$^{3,5}$.0$^{6,11}$) dodecan-1-ol. The cosmetic powder containing the material of Example XVII has a "patchouli cologne" fragrance with a warm patchouli-like character. The cosmetic powder produced using the material of Example XVI has a patchouli aroma with warm, woody, sweet and camphoraceous notes.

EXAMPLE XXII

LIQUID DETERGENT CONTAINING 11,12,12-TRIMETHYL-TETRACYCLO-(6.3.1.0$^{3,5}$.0$^{6,11}$) DODECAN-1-OL

Concentrated liquid detergents with a patchouli-like odor containing 0.2%, 0.5% and 1.2% of the product produced in accordance with the process of Example VII, 11,12,12-trimethyl-tetracyclo-(6.3.1.0$^{3,5}$.0$^{6,11}$) dodecan-1-ol are prepared by adding the appropriate quantity of 11,12,12-trimethyl-tetracyclo-(6.3.1.0$^{3,5}$.0$^{6,11}$) dodecan-1-ol to the liquid detergent known as P-87. The patchouli aroma of the liquid detergent increases with increasing concentration of the 11,12,12-trimethyl-tetracyclo-(6.3.1.0$^{3,5}$.0$^{6,11}$) dodecan-1-ol of this invention.

EXAMPLE XXIII

PREPARATION OF COLOGNE AND HANDKERCHIEF PERFUME

The composition of Example XVII is incorporated in a cologne having a concentration of 2.5% in 85% aqueous ethanol; and into a handkerchief perfume in a concentration of 20% (in 95% ethanol). The use of the composition of Example XVII affords a distinct and definite "patchouli cologne" aroma having a warm patchouli-like character to the handkerchief perfume and to the cologne.

EXAMPLE XXIV

COLOGNE AND HANDKERCHIEF PERFUME

The 11,12,12-trimethyl-tetracyclo-(6.3.1.0$^{3,5}$-.0$^{6,11}$) dodecan-1-ol produced by the process of Example XVI is incorporated into a cologne having a concentration of 2.5% in 85% ethanol; and into a handkerchief perfume in a concentration of 10% (in 95% ethanol). The 11,12,12-trimethyl-tetracyclo-(6.3.1.0$^{3,5}$.0$^{6,11}$) dodecan-1-ol produced in Example XVI affords a distinct and definite patchouli aroma with warm, woody, sweet and camphoraceous notes to the handkerchief perfume and to the cologne.

What is claimed is:

1. A substantially pure synthetically produced compound having the structure:

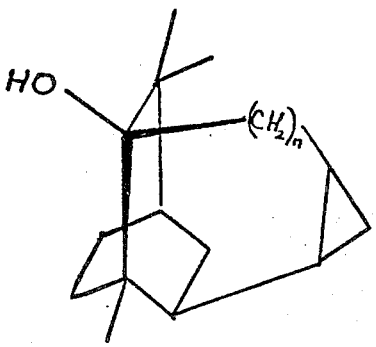

wherein $n$ is 0 or 1.

2. The compound of claim 1 wherein $n$ is 0.
3. The compound of claim 1 wherein $n$ is 1.
4. A compound having the structure:

5. A substantially pure synthetically produced compound which is synthetically produced 10,11,11-trimethyl-tetracyclo-(5.3.1.0$^{2,4}$.0$^{5,10}$) undecan-1-ol having a molecular weight of 206; the mass spectrum in decreasing order of intensity of 43, 109, 163, 178, 79, 55 and 91 m/e; an infrared absorption peak at a wave number of 3600 cm$^{-1}$ and a nuclear magnetic resonance spectrum having signals at 0.63, 0.78, 0.92, 0.97 and 1.02 ppm.

* * * * *